(12) United States Patent
Moskai

(10) Patent No.: US 8,859,973 B2
(45) Date of Patent: Oct. 14, 2014

(54) STRIP DEVICE AND METHOD FOR DETERMINING THE LOCATION AND TIME OF REACTION OF THE GAMMA QUANTA AND THE USE OF THE DEVICE TO DETERMINE THE LOCATION AND TIME OF REACTION OF THE GAMMA QUANTA IN POSITRON EMISSION TOMOGRAPHY

(75) Inventor: Pawel Moskai, Rybna (PL)

(73) Assignee: Uniwersytet Jagiellonski, Cracow (PL)

( * ) Notice: Subject to any disclaimer, the term of this patent is extended or adjusted under 35 U.S.C. 154(b) by 380 days.

(21) Appl. No.: 13/383,582

(22) PCT Filed: Jul. 16, 2010

(86) PCT No.: PCT/PL2010/000062
§ 371 (c)(1),
(2), (4) Date: Jan. 12, 2012

(87) PCT Pub. No.: WO2011/008119
PCT Pub. Date: Jan. 20, 2011

(65) Prior Publication Data
US 2012/0112079 A1 May 10, 2012

(30) Foreign Application Priority Data
Jul. 16, 2009 (PL) .......................................... 388555

(51) Int. Cl.
*G01T 1/20* (2006.01)
*G01T 1/164* (2006.01)
*G01T 1/29* (2006.01)

(52) U.S. Cl.
CPC .................................... *G01T 1/2985* (2013.01)
USPC ................................ 250/363.01; 250/363.03

(58) Field of Classification Search
USPC ..................................................... 250/363.03
See application file for complete search history.

(56) References Cited

U.S. PATENT DOCUMENTS

| | | | |
|---|---|---|---|
| 6,909,097 B2 * | 6/2005 | Schreiner et al. | 250/366 |
| 8,592,775 B2 * | 11/2013 | Workman et al. | 250/390.11 |
| 2005/0253073 A1 * | 11/2005 | Joram et al. | 250/363.03 |
| 2007/0057189 A1 * | 3/2007 | Jansen et al. | 250/363.09 |
| 2011/0272570 A1 * | 11/2011 | Xu et al. | 250/269.4 |
| 2011/0272587 A1 * | 11/2011 | Siegel et al. | 250/362 |

* cited by examiner

*Primary Examiner* — Christine Sung
(74) *Attorney, Agent, or Firm* — Mark M. Friedman

(57) ABSTRACT

The subject of the invention is a strip device and method for determining the place and time of the gamma quanta interaction as well as the use of the device for determining the place and time of the gamma quanta interaction in positron emission tomography.

8 Claims, 5 Drawing Sheets

STRIP DEVICE AND METHOD FOR DETERMINING THE LOCATION AND TIME OF REACTION OF THE GAMMA QUANTA AND THE USE OF THE DEVICE TO DETERMINE THE LOCATION AND TIME OF REACTION OF THE GAMMA QUANTA IN POSITRON EMISSION TOMOGRAPHY

The subject of the invention are a strip device and a method for determining the location and time of reaction of the gamma quanta and the use of the device to determine the location and time of reaction of the gamma quanta in positron emission tomography. More specifically the invention describes a solution to determine the spatial distribution of concentration of selected substances in the body and changes of their concentration in time.

Positron emission tomography is based on the determination of the spatial distribution of concentration of selected substances in the body and the changes of this concentration in time. To this end, the patient is administered pharmaceuticals marked with radioactive isotope emitting positrons. Radioactive marker is chosen so that it decays with the emission of positrons. The tomography uses the fact that the positron from the marker and electron from an atom of the body annihilate in contact with each other and their mass is converted into energy in the form of gamma quanta. Most frequently these are two gamma quanta flying back to back along the line with an exactly defined energy equal to 511 keV. The annihilation occurs typically only a few millimeters from the decay of the marker. This fact determines a natural limit of sharpness of the PET image. PET tomograph allows to locate the radioactive marker by measuring the direction of flight of the annihilation quanta. Radiation detectors are usually arranged in layers forming a ring around the patient. Currently, all commercial PET tomographs use inorganic scintillator material for detection. The energy of gamma quantum hitting the scintillator can be transferred partially or entirely to an electron of the material, which then produces flash of lights through ionization and deexcitation of atoms or molecules of the scintillator. These flashes are then converted to electrical pulses by photomultipliers connected to the scintillators. The number of photons generated in scintillator material is proportional to the energy that a quantum transferred to the electron. In turn, charge of electrical signal generated by photomultipliers is proportional to the number of photons incident on the photomultiplier window. For the energy of gamma quanta amounting to 511 keV there are two significant processes called photoelectric effect and Compton effect. In the first process gamma quantum transfers to the electron its entire energy, while in the second process only part of the energy is transferred depending also on the electron scattering angle. As a result of these processes, the spectrum of charge of registered signals consists of a continuous distribution corresponding to Compton effect and a peak corresponding to the photoelectric effect. Separation of this maximum allows to distinguish the cases where the annihilation quanta of energy 511 keV reached scintillator undisturbed from all the others cases. In the current tomographs one use scintillating crystals, made usually in size of about 5 cm×5 cm and which are additionally blazed into smaller pieces with dimensions of 0.5 cm×0.5 cm separated from each other with reflecting material. The end of each scintillating module is connected to photomultipliers which convert light into electrical impulses. This arrangement permits to determine, with the accuracy equal to the size of the small unit, the position where the gamma quantum reacted. Therefore, in the further analysis, one assumes that the quantum was absorbed in the middle of the unit. This causes the smearing of the image, the greater, the farther from the axis of the tomograph the annihilation occurred, and the larger is the scintillator module. One try to improve the image resolution by calculating the point of annihilation along the line of flight of the quanta by measurement of the time difference between the arrival of the gamma quanta to the detectors. In the literature this technique is known as TOF (time of flight), and tomographs which use the time measurements are termed PET-TOF. For efficient application of this technique one requires the time resolution in order of tens of picoseconds, unattainable in the current tomographs based on inorganic scintillators.

In Patent Application US 2006060823 (published at 2006 Mar. 26) an invention for a radiation detection scintillator using a flexible composite is described. This composite is created by the rapid mixing of dense, doped with rare earth elements oxyorthosilicate (eg, LSO:Ce, LSO:Sm, or GSO:Ce) with a binder which is transparent to the radiation emitted from the scintillator. Composites are uniform and can be made in large sizes and different shapes. Importantly, such a composite can emit radiation in the range of responses corresponding to the photomultiplier (400 nm) which increases the efficiency of the detector.

In Patent Application US 2008237470 (published at 2008 Oct. 2) a scintillation detector containing nanoparticles of scintillation component embedded in a matrix of plastic material is presented. The nanoparticles can be made from materials such as metal oxides, metal oxohalides, oxysulphides metals or metal halides. New ways of producing nanoparticles were developed in which particles can be coated by organic material or polymers before setting into a plastic matrix. The technique of matching the reflectance of the plastic matrix by the use of titanium dioxide nanoparticles was also developed. Scintillator can be joined with at least one photo-detector system forming a scintillation detector, which can be adapted for use in X-ray imaging systems, such as digital X-ray imaging, mammography, CT, PET or SPECT, or in safe detectors of radiation and detectors of the underground radiation.

In patent applications US 2008296505 (published at 2008 Dec. 4) and WO 2007082126 (published at 2007 Jul. 19) the way to reconstruct the image of the time of flight (TOF) is described. It includes obtaining of the outline of the investigated object in the test area (14) of imaging system (10). Events related to the radiation emitted from the object are recorded and converted into electronic data. The electrical signals corresponding to the incident radiation from outside the object are removed, thus the final images are reconstructed from the remaining electronic data.

In Patent Application US 2004173752 (published at 2004 Sep. 9) one has demonstrated that in case of certain hybrid organic/inorganic perovskite as the scintillator material, radiation is generated in the optical range at a rate of around subnanoseconds, and the same scintillator can be used as a detector of gamma radiation in PET tomography. PET scanner, according to the invention, contains a scintillator-based hybrid organic/inorganic perovskite compounds selected from the compounds of specific formula. Speed of response known for scintillators presently used in PET tomography is very limited, because there is a restriction of resolution obtained by this method. In order to solve this problem, one has estimated that the scintillator response rate should be approximately 0.1 ns. The development of such scintillator allowed to limit temporal resolution obtained with this method. In the described application methods of manufacture and the composition of such scintillators on the order of several cubic centimeters are given. However, in order to achieve spatial resolution along the lines of response, that would be on the order of the natural uncertainty originating from the positron absorption in the body of the patient, the required time resolution should be better than 50 ps and the economic imaging of the entire human body needs fast scintillators on the order of meters in size.

In the Patent Application EP 2047297 (published at 2008 Apr. 21) PET tomograph (100) based on time of flight measurement is presented. It includes the detector (106), system (120) of data acquisition, system of compliance (122) and reconstructing unit (129). Elements for imaging affect the time resolution of the system (100) so that the positron data, which are collected along different lines of response are characterized by different timing resolutions. These time resolutions are used for determining the position of registered events along the corresponding lines of response.

Despite the above described research focused on solutions for determination of the place and time of the interaction of gamma quanta used in positron emission tomography, there is a continuing need for an effective solution for detection of radiation using a plastic scintillator doped with atoms of high atomic number, which would allow to obtain time resolutions needed for the effective application of TOF techniques, as well as for substantial reductions in the cost of production of PET tomographs due to the relatively easy possibility to produce organic scintillators in any size.

The purpose of this invention is to provide resources that could be used to produce solutions for the determination of the place and time of reacting gamma quanta used in positron emission tomography.

The realization of such a particular purpose, and solution of problems described in the state-of-art techniques associated with measuring of time of flight and with limitations of the obtained time resolution, have been achieved in the present invention.

The subject matter of invention is a device for determining the place and time of the gamma quanta interaction built out of scintillation chamber which is made of plastic scintillator strips, preferably doped with atoms of atomic number at least 50. The surfaces of scintillation strips reflect photons incident to the surface from the inside at an angle greater than the so-called boundary angle, then photons resulting from absorption of the quanta in the scintillator material, which reach to the front or the rear edge of the strip are conducted through optical connectors to the photomultipliers. The point of impact of the gamma quantum in a plane perpendicular to the axis of strips is determined from the position of the module that registered the signal, while the position along the scintillation chamber is determined based on the time difference measured in the front and rear photomultipliers. The time when quantum interacted in a scintillator strip is calculated as the arithmetic mean from the time measured in the front and rear photomultipliers. Then the determined set of reconstructed lines LOR and the location of annihilation points along these lines provide a tomographic picture.

Preferably, the optical connector material is selected so that its refractive index is most similar to the refractive index of scintillator, while similar in value refractive indexes minimize the reflection of photons in the place of connection.

Preferably, the resulting light pulses are converted into electrical signals by means of photomultipliers optically connected with scintillators. The photomultipliers are attached to the mounting plate that is fixed to the housing and shelter the entire unit.

Preferably, the optical connection of the scintillator to the photomultiplier is done by means of silicon gels or gums directly or via light-guides, and the strips are separated from each other optically, preferably using light-tight foils and also that each bar is individually wrapped.

Preferably, when the device is presented in FIGS. 1 to 5.

The next subject of the invention is a method for determining the place and time of the gamma quanta interaction, characterized in that the surfaces of scintillation strips reflect the photons falling on the inside surface at an angle greater than the so-called border angle, while the strips are separated from each other optically, then photons resulting from absorption of the quanta in the scintillator material, which reach the front or the rear edge of the strip are conducted through optical connectors to the photomultipliers. The point of impact of the gamma quantum in a plane perpendicular to the axis of strips is determined from the position of the module that registered the signal, while the position along the scintillation chamber is determined based on the time difference measured in the front and rear photomultipliers. The time when quantum interacted in a scintillator strip is calculated as the arithmetic mean of times measured in the front and rear photomultipliers, then on the basis of amplitudes of signals in the photomultipliers on both sides one determines the energy of the electron colliding with gamma quantum, after which one identifies the LOR line on the basis of coordinates of the reaction point for both gamma quanta and place of annihilation along the LOR based on the measured time differences, after which the determined set of reconstructed lines LOR and the location of annihilation points along these lines provide a tomographic picture.

Preferably, the electronic circuit converts the amplitude and time of emergence of signals to digits, which are sent to the computer in binary form, where on its basis the distribution of density of radioactive marker in the patient's body is reconstructed.

Preferably, when the method is used in positron emission tomography.

Another object of the invention is the use of the device described above in positron emission tomography.

The attached figure allows for a better explanation of the substance of a solution, where:

The various markings on the figures indicate, respectively:
1—Scintillation chamber for the examination of the patient, 2—housing of the chamber and photomultipliers, 3—housing for electronic circuits, 4—computer for the reconstruction of the tomographic image, 5—monitor, 6—printer, 7—a platform that allows the patient to move into the scintillation chamber, 8—scintillation strip, 9—foil, 10—light-guide, 11—photomultiplier, 12—voltage divider, 13—power cable, 14—signal cable, 15—plate for mounting photomultipliers, 16—holes for the photomultiplier tubes, 17—plastic cover, 18—signal splitter, 19—discriminator, 20—coincidence system, 21—delay line, 22—TDC—time-to-digit converter, 23—ADC—charge-to-digit converter, 24—signal cables.

For a better understanding of the solutions below an exemplary embodiment of the invention is presented.

EXAMPLE

Figure 1:
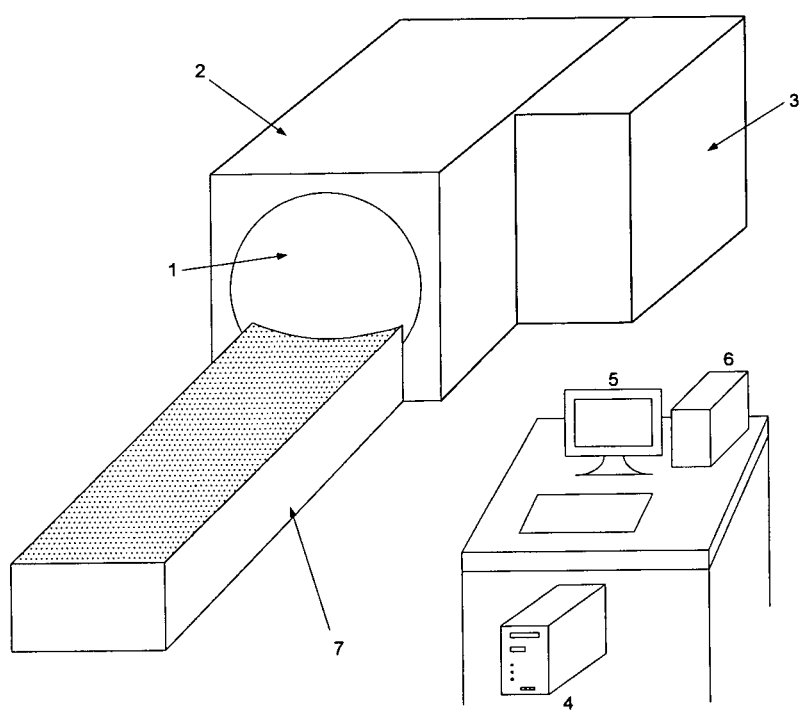
FIG. 1 shows a general scheme of the device—strip tomograph.

FIG. 1 shows a general scheme of the device, which consists of a scintillation chamber (1), into which the patient, after inserting the radio-pharmaceuticals, is placed. Gamma-quanta resulting from the decay of radioactive marker in the patient's body produce light flashes in the scintillation chamber. The resulting light pulses are converted into electrical signals by means of photomultipliers located at the front and rear part between the scintillation chamber and casing of the entire unit (2). The signals from the photomultipliers are sent using cables to the electronics located in the housing (3) sticking to the scintillation chamber casing. The electronic circuit converts the amplitude and time of emergence of signals to digits, which are sent to the computer in binary form (4), where on its basis the distribution of density of radioactive marker in the patient's body is reconstructed. This image can be viewed on the screen (5), printed (6), or saved to disk in the computer. In order to perform the examination the patient is placed on the platform (7), which can be slipped into the scintillation chamber (1) lined from the patient's side with plastic cover.

Figure 2:
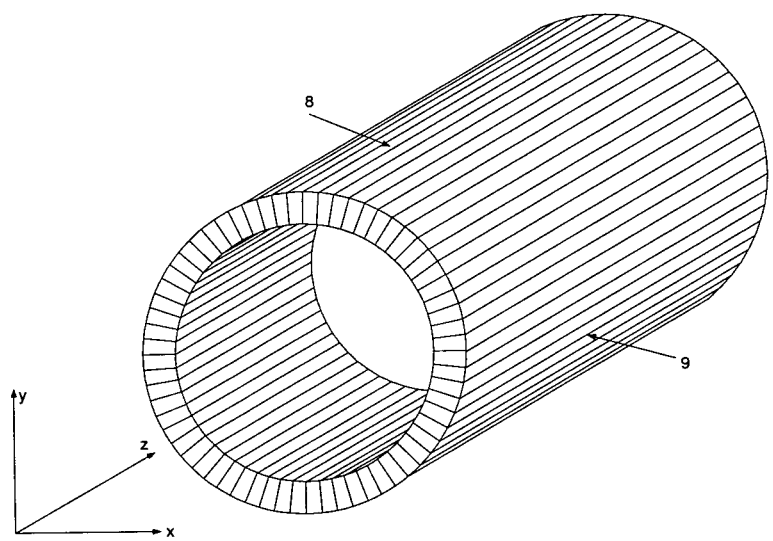
FIG. 2 shows an example of the arrangement of strips 8 in the tomograph.
Figure 3:
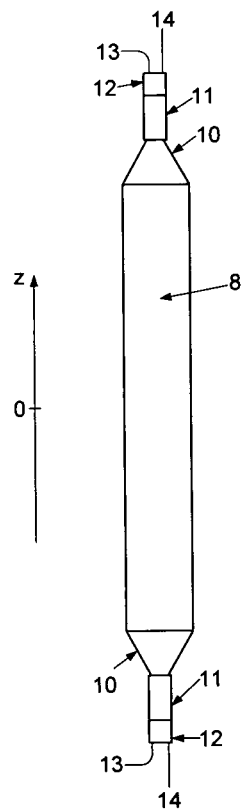
FIG. 3 shows the scheme of a single detector module.

Scintillation chamber (1) consists of strips of plastic scintillator doped with atoms of high atomic number, in this case lead. FIG. 2 shows an exemplary arrangement of scintillation strips (8). Surfaces of the scintillation strips should be cutted with diamond blade, or polished in order to reflect photons incident to the surface from the inside at an angle greater than the so-called boundary angle. Strips are separated optically by a light-tight foil (9). One way to do that is to wrap with the foil each strip separately. Photons of light, resulting from absorption of gamma quantum in the scintillator material, which reach to the front or the rear edge of the strip are conducted through light-guide (10) to photomultipliers (11). Schematic view of a single detector module is shown in FIG. 3. Optical light-guides (10) are attached to the scintillation strips with optical glue which refractive index is close to the refractive index of the material from which the scintillators are made. It should be noted that the light-guide material should be selected so that its refractive index is most similar to the refractive index of scintillator. Similar coefficients of light minimize the reflections of photons in the connection region. Combining the light-guide to the photomultiplier (11) can be obtained by appropriate gel or silicon rubber.

Voltage is distributed to the photomultiplier dynodes (11) using voltage dividers (12), which must be properly matched to the type of photomultiplier. The voltage divider is supplied using voltage cables (13) connected with the power supply located in the housing of the electronics labeled with the number (3) in FIG. 1. The signals from the photomultipliers (11) are delivered to the electronics by signal cables (14).

Figure 4A:
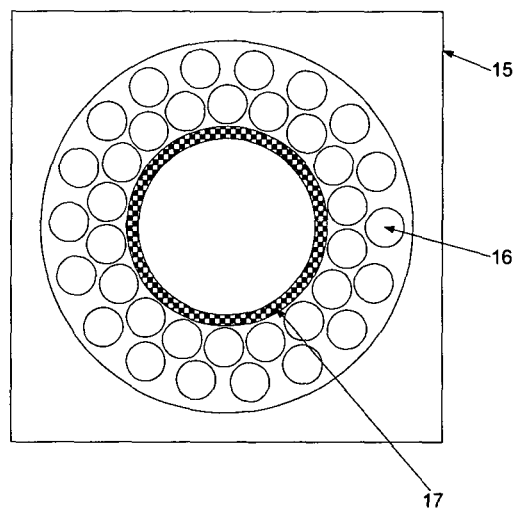
FIG. 4 shows a sample mounting of photomultipliers 11.
Figure 4B:
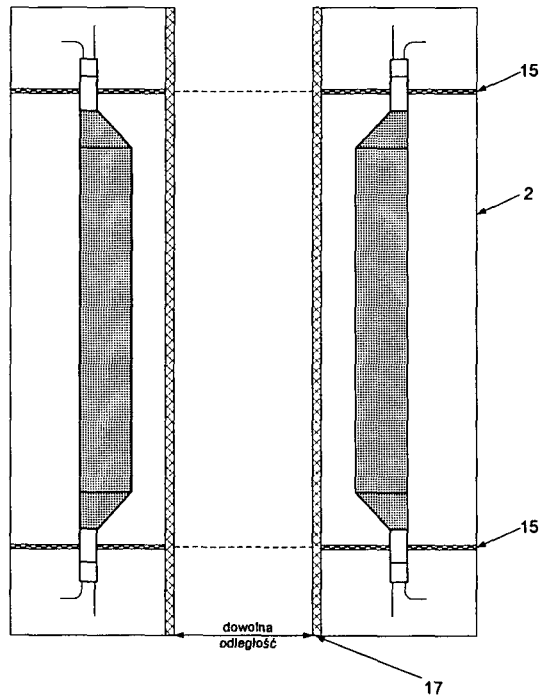

In FIG. 4 an example of photomultipliers mounting is shown. Photomultipliers are attached to the mounting plate (15), which is in turn fastened to the housing of the entire device (2). Plate to maintain photomultipliers (15) have openings (16), whose size and shape is adjusted to the size and shape of the casing of photomultipliers, and the relative setup and distance can be optimized in terms of required resolution, thickness of the strips and costs of the device. From the patient side a plastic cover is seen (17).

Figure 5:
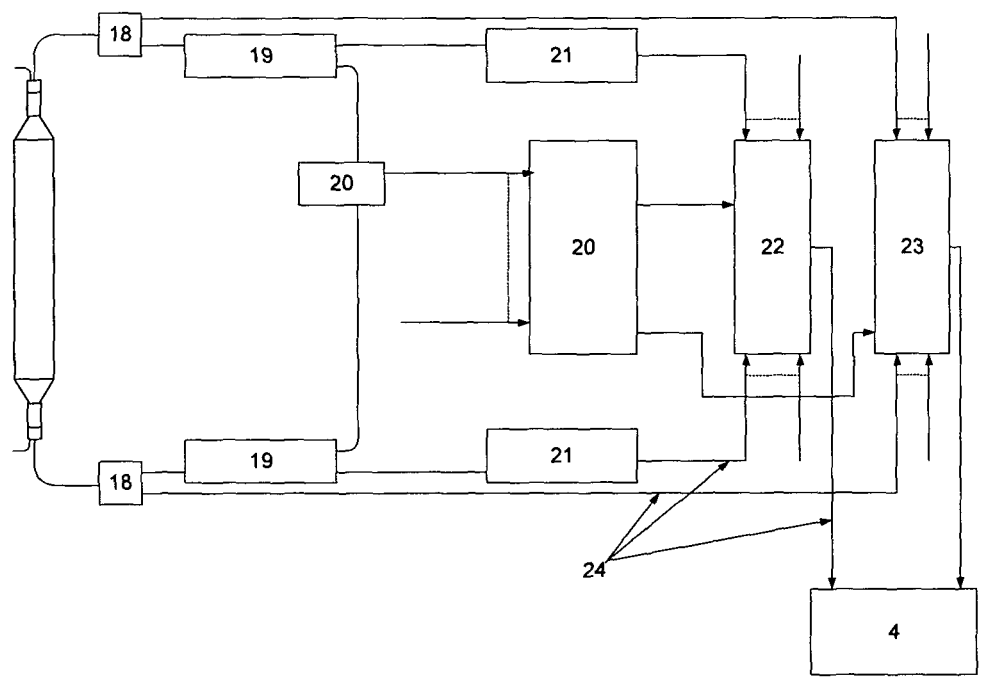
FIG. 5 shows an example of the logic diagram of the electronic system that allows to obtain information about the amplitude and time of impulses generated by photomultiplier.

FIG. 5 shows an exemplary logic diagram of the electronic system that allows to obtain information about the amplitude and time of electric pulses generated by photomultipliers. These in turn are closely linked in time and amplitude of light signals reaching the photomultipliers.

A program to analyze the data in the first step would perform selection of these events, for which signals were registered in at least two strips with a proper relative distance. At the same time signals in each strip would have to be recorded in both, front and rear photomultipliers. In addition further treatment would be applied only to those signals that are within a fixed time interval (several nanoseconds). Then location of the reaction along the chamber (coordinate z) is determined on the basis of time difference between the signal reaching the front and rear of the strip according to the formula:

$$z = beta * Delta(t)/2 + C1 = beta * (t\_front - t\_back)/2 + C1,$$

where beta is the speed of light signal in the scintillator strip, and C1 is a calibration constant. Determination of the point of impact of gamma quantum along the scintillation chamber on the basis of time measurement is the main feature of this invention. The point of impact in a plane perpendicular to the axis of the strips (xy in FIG. 2) is determined from the location of the module that registered the signal. Time of the interaction of quantum in the scintillation strip is determined as the arithmetic mean from the time measured in the front and rear photomultipliers:

$$t = (t\_front + t\_back)/2 + C2,$$

where C2 is a calibration constant.

Knowledge of the signal amplitudes in photomultipliers on both sides allows to calculate the energy of the electron which reacted with the gamma quantum.
For the calculation following formula can be used in the first approximation:

$$E = C3 * (A\_front + A\_back),$$

where C3 is a calibration constant.

Knowing the coordinates r=(x, y, z) for the reaction point for both gamma quantum r1 and r2 lines of LOR can be determined.

Knowing r1, r2, t1 and t2 one can calculate the place of annihilation along the LOR line using the formula Delta (LOR)=(t2−t1)/2*c, where c is the speed of light.

Consequently, the point of annihilation is determined by the following formula:

$$\vec{r_a} = \frac{\vec{r_1} + \vec{r_2}}{2} + \frac{\vec{r_1} - \vec{r_2}}{|\vec{r_1} - \vec{r_2}|} \cdot \Delta LOR$$

The described device provides a set of reconstructed LOR lines and the location of annihilation points along these lines. Based on these data the tomographic image is obtained by imaging reconstruction techniques.

The proposed solution allows to build a device for registering of gamma quanta in positron emission tomography, whose cost does not increase significantly with the size of the scanner, because the extension of the chamber to record the image is related only to the increase of the length of scintillation strips while keeping the number of photomultipliers, light-guides, and the number of electronic circuits for signal processing.

The invention claimed is:

1. A strip device for determining a location and a time of a gamma quantum reaction, comprising a scintillation chamber, wherein said scintillation chamber has an internal cylindrical surface at which there are arranged a plurality of scintillator strips, wherein surfaces of said scintillator strips are configured to reflect photons falling on said surfaces from inside of said scintillation chamber at an angle greater than a boundary angle, each scintillator strip being optically connected to photomultipliers for receiving, via light-guides, photons of light, resulting from a gamma quantum absorbed in a scintillator material of said scintillator strip, wherein an energy of said gamma quantum is transferred entirely to an electron of said scintillator material via a photoelectric effect or partially via a Compton effect, which reach a front edge or a rear edge of said scintillator strip, and wherein said device further comprises an electronic system for determining a location of annihilation points along lines of response, said electronic system being configured to:
  (a) select events for which signals are registered within a fixed time interval in a pair of said scintillator strips spaced with a relative distance, and
  (b) for each selected event,
    i) determine a point of impact of said gamma quantum in a plane perpendicular to a longitudinal axis of said scintillator strip from a position of said scintillator strip that registered said signal, and
    ii) for each scintillator strip of said pair of scintillator strips which registered said signal for said selected event:
      (1) determine an impact position in said scintillator strip along said scintillation chamber on a basis of a time difference (t_front-t_back) between a front time (t_front) measured in a front photomultiplier and a back time (t_back) measured in a rear photomultiplier of said scintillator strip,
      (2) determine an interaction time (t1, t2) when said gamma quantum interacted in each scintillator strip as an arithmetic mean of said front time (t_front) measured in said front photomultiplier and said back time (t_back) measured in said rear photomultiplier of each scintillator strip,
      (3) determine an energy of an electron of said scintillator material to which the energy of said gamma quantum was transferred by means of the Compton effect or the photoelectric effect, on a basis of amplitudes of said signals measured in said photomultipliers on both sides of said scintillator strips,
    iii) determine a line of response on a basis of said determined impact positions in said two scintillator strips of said pair of scintillator strips,
    iv) determine a place of annihilation along said line of response based on said determined interaction times (t1, t2),
  (c) provide a tomographic image from a set of said determined lines of response and said places of annihilation along said lines of response determined for each of said selected events, and
  (d) wherein said scintillator strips are made of plastic doped with atoms with atomic number of at least 50.

2. The device according to claim 1, wherein a material of said light-guides has a refractive index equal to a refractive index of said scintillator material.

3. The strip device according to claim 1, wherein said photomultipliers are optically connected with said light-guides, and said photomultipliers are attached to a mounting plate which is attached to a housing of said strip device.

4. The strip device of claim 1, wherein said light-guides are coupled to said photomultipliers by a gel or a silicon rubber.

5. The strip device according to claim 1, wherein said scintillator strips are separated from each other optically.

6. The strip device according to claim 1, wherein each scintillator strip is wrapped separately.

7. A method for determining a location and a time of a gamma quanta reaction in a device providing a scintillation chamber, wherein said scintillation chamber has an internal cylindrical surface at which there are arranged a plurality of scintillator strips, wherein surfaces of said scintillator strips are configured to reflect photons falling on said surfaces from inside of said scintillation chamber at an angle greater than a boundary angle, while said scintillator strips are separated from each other optically, each scintillator strip being optically connected to photomultipliers for receiving, via light-guides photons resulting from absorption of a gamma quantum absorbed in a scintillator material of said scintillator strip, wherein an energy of said gamma quantum is transferred entirely to an electron of said scintillator material via a photoelectric effect or partially via a Compton effect, which reach a front edge or a rear edge of said scintillator strip, the method comprising locating annihilation points along lines of response by:
  (a) selecting events for which signals are registered within a fixed time interval in a pair of said scintillator strips spaced with a relative distance, and
  (b) for each selected event,
    i) determining a point of impact of said gamma quantum in a plane perpendicular to a longitudinal axis of said scintillator strip from a position of said scintillator strip that registered said signal, and
    ii) for each scintillator strip of said pair of scintillator strips which registered said signal for said selected event:
      (1) determining an impact position in said scintillator strip along said scintillation chamber on a basis of a time difference (t_front-t_back) between a front time (t_front) measured in a front photomultiplier and a back time (t_back) measured in a rear photomultiplier of said scintillator strip,
      (2) determining an interaction time (t1, t2) when said gamma quantum interacted in each scintillator strip as an arithmetic mean of said front time (t_front) measured in said front photomultiplier and said back time (t_back) measured in said rear photomultiplier of each scintillator strip,
      (3) determining an energy of an electron of said scintillator material to which the energy of said gamma quantum was transferred by means of the Compton effect or the photoelectric effect, on a basis of amplitudes of said signals measured in said photomultipliers on both sides of said scintillator strips;
    iii) determining a line of response on a basis of said determined impact positions in said two scintillator strips of said pair of scintillator strips,
    iv) determining a place of annihilation along said line of response based on said determined interaction times (t1, t2),
  (c) providing a tomographic image from a set of said determined lines of response and said places of annihilation along said lines of response determined for each of said selected events, and
  (d) wherein said scintillator strips are made of plastic doped with atoms with atomic number of at least 50.

8. The method according to claim 7, further comprising sending the amplitudes of said signals measured in said photomultipliers and said interaction times in a binary form to a computer and reconstructing in said computer a distribution of density of a radioactive marker in a patient's body.

* * * * *

UNITED STATES PATENT AND TRADEMARK OFFICE
CERTIFICATE OF CORRECTION

PATENT NO. : 8,859,973 B2
APPLICATION NO. : 13/383582
DATED : October 14, 2014
INVENTOR(S) : Pawel Moskal It is certified that error appears in the above-identified patent and that said Letters Patent is hereby corrected as shown below:

Title page
(75) Inventor, should be corrected as follows:
Change:
-- Pawel Moskai --
to
"Pawel Moskal"

Signed and Sealed this
Twenty-sixth Day of July, 2016

Michelle K. Lee
*Director of the United States Patent and Trademark Office*